United States Patent [19]

Kishita et al.

[11] Patent Number: 5,523,441

[45] Date of Patent: Jun. 4, 1996

[54] FLUOROCARBON GROUP-CONTAINING ORGANOSILANE COMPOUND

[75] Inventors: Hirofumi Kishita; Noriyuki Koike; Hideyoshi Yanagisawa; Toshio Takago, all of Gunma-ken, Japan

[73] Assignee: Shin-Etsu Chemical Co., Ltd., Tokyo, Japan

[21] Appl. No.: 383,376

[22] Filed: Feb. 3, 1995

[30] Foreign Application Priority Data

Feb. 4, 1994 [JP] Japan .................................. 6-12426
Feb. 4, 1994 [JP] Japan .................................. 6-12443

[51] Int. Cl.$^6$ ................................................. C07F 7/10
[52] U.S. Cl. ........................... 556/413; 556/423; 556/424
[58] Field of Search ............................. 556/413, 423, 556/424

[56] References Cited

U.S. PATENT DOCUMENTS

| | | | |
|---|---|---|---|
| 3,012,006 | 12/1961 | Holbrook et al. | 556/424 |
| 3,639,156 | 2/1972 | Pittman et al. | 556/423 |
| 3,720,624 | 3/1973 | Haszeldine et al. | 556/413 |
| 3,772,346 | 11/1973 | Hess | 556/413 |
| 3,944,587 | 3/1976 | Katsushima et al. | 556/424 |
| 5,124,467 | 6/1992 | Rodgers et al. | 556/413 X |

*Primary Examiner*—Paul F. Shaver
*Attorney, Agent, or Firm*—Millen, White, Zelane, & Branigan

[57] ABSTRACT

Disclosed is a novel polyfluorocarbon group-containing alkoxy silane compound useful as a silane coupling agent as represented by the general formula $$A-R_f-(-CH_2-)_n-NH-R^1-SiR_3,$$

in which each R is, independently from the others, a monovalent hydrocarbon group having 1 to 10 carbon atoms or an alkoxy group having 1 to 6 carbon atoms with the proviso that at least one of the three groups denoted by R is an alkoxy group, $R^1$ is a divalent hydrocarbon group having 1 to 10 carbon atoms, A is a monovalent group selected from the class consisting of a hydrogen atom, a fluorine atom, an aminomethyl group and a 2-aminoethyl group, $R_f$ is a polyfluorinated alkylene group with 1 to 20 carbon atoms or a polyfluorinated etherified alkylene group with 2 to 20 carbon atoms having at least one oxygen atom between two carbon atoms of an alkylene group forming an ether linkage, at least two of the hydrogen atoms therein being substituted by fluorine atoms, and the subscript n is 1 or 2.

7 Claims, 2 Drawing Sheets

FLUOROCARBON GROUP-CONTAINING ORGANOSILANE COMPOUND

The present invention relates to a novel fluorocarbon group-containing organosilane compound or, more particularly, to a fluorocarbon group-containing organosilane compound having usefulness as a silane coupling agent and not known in the prior art nor described in any literature.

BACKGROUND OF THE INVENTION

As is well known, it is an established application of carbon-functional organosilane compounds of various types that the silane compound is used as a so-called silane coupling agent which enhances compatibility and adhesion between different materials such as an inorganic and organic materials to be combined. A class of the carbon-functional organosilane compounds having an activity as a silane coupling agent includes those having an amino group or N-substituted amino group bonded to the silicon atom of the silane compound through a divalent hydrocarbon group. One of typical amino group-containing silane compounds is 3-aminopropyl trimethoxy silane and this compound is widely used as a silane coupling agent for the surface treatment of plastic articles and synthetic fibers and for adhesion promotion of sealants and adhesives. Though quite effective in respect of the activity as a silane coupling agent, these amino group-containing silane compounds have various disadvantages and problems. For example, conventional amino-functional silane coupling agents in general have relatively low water-resistance so that, when such a silane coupling agent is used as an adhesion promotor in a silicone rubber composition, the adhesive bonding strength between the cured silicone rubber and the substrate surface on which the composition has been cured is decreased in the lapse of time by immersion in water. When the amino-functional silane coupling agent is used as a surface-treatment agent for silicon dioxide fillers and the like to be compounded in a sealant such as those based on an epoxy resin used in electric and electronic parts, the moistureproofing effect of the sealant is sometimes not high enough.

Accordingly, it is eagerly desired to develop an amino group-containing organosilane compound having excellent activity as a silane coupling agent but free from the disadvantages and problems in the conventional amino group-containing silane compounds mentioned above. The inventors have conducted extensive investigations to discover or uncover a silane compound to meet the above mentioned requirements including synthetic preparation of various amino group-containing organosilane compounds and testing thereof as a silane coupling agent. The organosilane compounds synthesized in the course of this synthetic work included several novel silane compounds not known in the prior art nor described in any literature, of which the fluorocarbon group-containing alkoxy silane compounds proposed here were found to be particularly useful as a silane coupling agent.

SUMMARY OF THE INVENTION

Thus, the present invention, which has been completed as a result of the above mentioned investigations, provides a novel fluorocarbon group-containing alkoxy silane compound represented by the general formula $$A-R_f-(-CH_2-)_n-NH-R^1-SiR_3, \quad (I)$$

in which each R is, independently from the others, a monovalent hydrocarbon group having 1 to 10 carbon atoms or an alkoxy group having 1 to 6 carbon atoms with the proviso that at least one of the three groups denoted by R is an alkoxy group, $R^1$ is a divalent hydrocarbon group having 1 to 10 carbon atoms, A is a monovalent group selected from the class consisting of a hydrogen atom, a fluorine atom, an aminomethyl group and a 2-aminoethyl group, $R_f$ is a polyfluorinated alkylene group with 1 to 20 carbon atoms or a polyfluorinated etherified alkylene group with 2 to 20 carbon atoms having at least one oxygen atom between two carbon atoms forming an ether linkage, at least two of the hydrogen atoms therein being substituted by fluorine atoms, and the subscript n is 1 or 2.

DETAILED DESCRIPTION OF THE PREFERRED EMBODIMENTS

Figure 1:
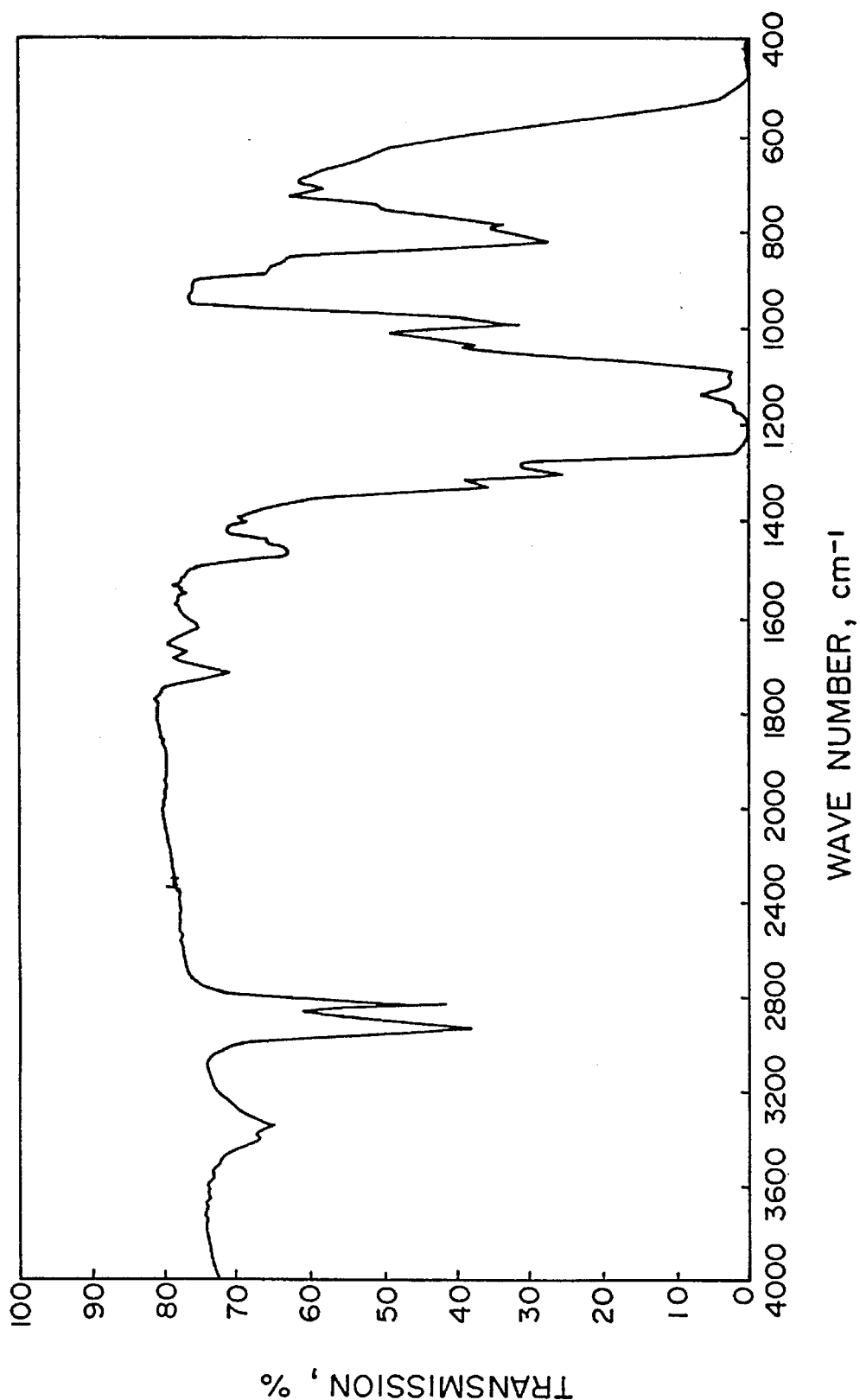
FIGS. 1 and 2 are each an infrared absorption spectrophotometric spectrum of the compound prepared in Examples 1 and 2, respectively.

As is described above, the fluorocarbon group-containing alkoxy silane compound of the invention is represented by the general formula (I) given above and characterized by the specific monovalent group of the formula $$A-R_f-(-CH_2-)_n-NH-R^1-, \quad (II)$$

bonded to the silicon atom, in which each symbol has the meaning as defined above, the other three silicon-bonded groups denoted by R being rather conventional but including at least one alkoxy group.

In the general formula (I), each of the three groups denoted by R is, independently from the others, a monovalent hydrocarbon group having 1 to 10 carbon atoms exemplified by alkyl groups such as methyl, ethyl, n-propyl, isopropyl, n-butyl, isobutyl, tert-butyl, hexyl, cyclohexyl, octyl and decyl groups, alkenyl groups such as vinyl, allyl, propenyl, isopropenyl, butenyl, isobutenyl, hexenyl and cyclohexenyl groups, aryl groups such as phenyl and tolyl groups and aralkyl groups such as benzyl and 2-phenylethyl groups or an alkoxy or alkoxy-substituted alkoxy group having 1 to 6 carbon atoms exemplified by methoxy, ethoxy, propoxy, butoxy, hexoxy, methoxymethoxy, methoxyethoxy, ethoxymethoxy and ethoxyethoxy groups. It is essential that at least one of the three groups denoted by R is an alkoxy group defined above. It is preferable that two or, more preferably, all of the groups R are alkoxy groups when the intended application of the inventive silane compound is as a silane coupling agent.

In the general formula (II) representing the other silicon-bonded group characteristic in the inventive silane compound, $R^1$ is a divalent hydrocarbon group having 1 to 10 carbon atoms exemplified by alkylene groups such as methylene, ethylene, propylene, methylethylene, butylene, hexylene, octylene and decylene groups, arylene groups such as phenylene and methylphenylene groups, and combinations of alkylene groups and arylene groups such as those of the formulae $-CH_2-Pn-$ and $-CH_2-Pn-CH_2CH_2-$, Pn being a 1,4-phenylene group, though not particularly limitative thereto while the subscript n is 1 or 2 so that the polyfluorinated group $R_f$ is bonded to the nitrogen atom through a methylene or ethylene linkage. The group denoted by A is an end-blocking group at the other terminal of the divalent polyfluorinated group $R_f$ and is selected from the class consisting of a hydrogen atom, a fluorine atom, an aminomethyl group and a 2-aminoethyl group.

The divalent group denoted by $R_f$ is a polyfluorinated alkylene or etherified alkylene group having not more than 20 carbon atoms. The word "polyfluorinated" means that at least two of the hydrogen atoms in the (etherified) alkylene group are substituted by fluorine atoms. It is preferable that all of the hydrogen atoms in the (etherified) alkylene group are substituted by fluorine atoms or, in other words, the polyfluorinated group is a perfluorinated group when the intended application of the inventive silane compound is as a silane coupling agent. Further, the term "etherified" alkylene group here implied means an alkylene group of which at least one pair of carbon atoms are bonded together through an oxygen atom to form an ether linkage therebetween.

Examples of the divalent group denoted by $R_f$ include those expressed by the following formulas: $-CF_2-$; $-CF_2CF_2-$; $-CF_2CF_2CF_2-$; $-CF_2CF_2CF_2CF_2-$; $-CF_2CF_2CF_2CF_2CF_2-$; $-CF_2CF_2CF_2OCF(CF_3)-$; $-CF_2CF_2CF_2OCF(CF_3)CF_2OCF(CF_3)-$; $-CF_2CF(CF_3)OCF(CF_3)-$; $-CF(CF_3)OCF_2CF_2OCF(CF_3)-$; $-CF(CF_3)OCF_2CF_2CF_2CF_2OCF(CF_3)-$; $-CF_2OCF_2CF_2OCF_2-$; and the like, though not particularly limitative thereto.

As is readily understood from the above given description, the novel fluorocarbon group-containing alkoxy silane compounds proposed by the present invention include a great number of compounds depending on the selection of the groups denoted by R, $R^1$, A and $R_f$ and the value of the subscript n, all of which are novel. Following are only a few of the structural formulae expressing the inventive novel fluorocarbon group-containing alkoxy silane compounds:

$CF_3(CF_2)_pCH_2NH(CH_2)_3SiR^2_{3-m}(OR^3)_m$;

$CF_3CF_2CF_2OCF(CF_3)-[-CF_2OCF(CF_3)-]_q-CH_2NH(CH_2)_3--SiR^2_{3-m}(OR^3)_m$;

$H_2NCH_2(CF_2)_rCH_2NH(CH_2)_3SiR^2_{3-m}(OR^3)_m$; and $H_2NCH_2CF(CF_3)OCF_2CF_2OCF(CF_3)CH_2NH(CH_2)_3--SiR^2_{3-m}(OR^3)_m$;

in which $R^2$ and $R^3$ are each, independently from the other, a methyl group or an ethyl group, the subscript m is 2 or 3, the subscript p is 0 or a positive integer not exceeding 4, the subscript q is 0 or 1, and the subscript r is 2, 3 or 4.

The above defined and exemplified fluorocarbon group-containing alkoxy silane compounds of the invention can be synthetically prepared by utilizing the dehydrohalogenation reaction between an amino group and a halogenated hydrocarbon group in the presence of an acid acceptor. Namely, an amino compound represented by the general formula

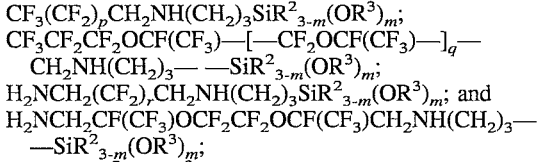

$$A-R_f-(-CH_2-)_n-NH_2, \quad (III)$$

in which each symbol has the same meaning as defined above, and a halogenated hydrocarbyl alkoxy silane compound represented by the general formula $$X-R^1-SiR_3, \quad (IV)$$

in which X is a halogen atom and each of the other symbols has the same meaning as defined above, are mixed together and the mixture is heated at an elevated temperature so that a dehydrohalogenation reaction takes place between the amino group in the first reactant of the formula (III) and the halogenated hydrocarbyl group $X-R^1-$ in the second reactant of the formula (IV) to form the fluorocarbon group-containing alkoxy silane compound of the general formula (I) along with formation of a hydrogen halide HX as a by-product of the reaction, which should be captured by an acid acceptor.

The halogen atom X in the second reactant of the formula (IV) can be an atom of chlorine, bromine or iodine of which bromine and iodine are preferred in view of the higher reactivity than chlorine in the dehydrohalogenation reaction. The above mentioned acid acceptor includes various kinds of amine compounds such as triethyl amine, pyridine, triethylene diamine and the like. The dehydrohalogenation reaction proceeds between equimolar amounts of the first reactant of the formula (III) and the second reactant of the formula (IV) so that the reaction mixture can be prepared by mixing equimolar amounts of the reactants with addition of an acid acceptor. It is sometimes preferable, however, that the amino compound as the first reactant of the formula (III) is used in an excessive amount over the equimolar amount relative to the second reactant of the formula (IV) so that the excess of the amino compound serves as the acid acceptor and addition of a separate acid acceptor can be decreased or omitted. For example, up to 6 moles or, preferably, up to 4 moles of the amino compound of the formula (III) are combined per mole of the second reactant of the formula (IV). If necessary, the reaction mixture can be diluted by the addition of an organic solvent such as methyl alcohol, ethyl alcohol, toluene, xylene, ethylbenzene and the like.

The reaction mixture is heated at a temperature in the range from 50 to 120° C., for example, under reflux of the solvent. The reaction is complete usually within 2 to 70 hours. After completion of the reaction, the reaction mixture is admixed with an alkali metal alcoholate such as sodium methylate and then freed from the precipitated salts by filtration followed by distillation of the filtrate to give the desired fluorocarbon group-containing alkoxy silane compound of the invention in a good yield.

The amino compound as the first reactant of the formula (III) is selected depending on the polyfluorinated group $R_f$, terminal group A and subscript n in the desired silane compound. Examples of the compound, when A is a fluorine atom, include those expressed by the following formulae: $CF_3CH_2NH_2$; $CF_3CF_2CH_2NH_2$; $CF_3CF_2CF_2CF_2CH_2NH_2$; $CF_3CF_2CF_2CF_2CH_2CH_2NH_2$; $CF_3CF_2CF_2OCF(CF_3)CH_2NH_2$; $CF_3CF_2CF_2OCF(CF_3)CF_2OCF(CF_3)CH_2NH_2$; and $(CF_3)_2CFOCF(CF_3)CH_2NH_2$.

When the terminal group A is an aminomethyl group, the amino compound as the first reactant of the formula (III) is a diamine compound and examples of the compound include those expressed by the following formulae:

$H_2NCH_2CF_2CF_2CH_2NH_2$; $H_2NCH_2CF_2CF_2CF_2CF_2CH_2NH_2$;

$H_2NCH_2CF(CF_3)OCF_2CF_2OCF(CF_3)CH_2NH_2$;

$H_2NCH_2CF(CF_3)OCF_2CF_2CF_2CF_2OCF(CF_3)CH_2NH_2$;

$H_2NCH_2CF_2OCF_2CF_2OCF_2CH_2NH_2$; and

$H_2NCH_2CF_2O(CF_2)_uO(CF_2CF_2)_vOCF_2CH_2NH_2$, in which u and v are each a positive integer with the proviso that u+2v does not exceed 18. These polyfluorinated diamine compounds can be prepared according to a known method disclosed, for example, in U.S. Pat. No. 2,515,246.

The halogenated hydrocarbyl alkoxy silane as the second reactant of the formula (IV) is exemplified by: 3-halogenopropyl trimethoxy silane; 3-halogenopropyl triethoxy silane; 3-halogenopropyl methyl dimethoxy silane; 3-halogenopropyl methyl diethoxy silane; halogenomethyl trimethoxy silane; 6-halogenohexyl trimethoxy silane; 10—halogenodecyl trimethoxy silane; 2-(4-halogenomethylphenyl)ethyl trimethoxy silane and the like, in which the halogen is chlorine, bromine or iodine or, preferably, bromine or iodine.

In the following, examples are given to illustrate the polyfluorocarbon group-containing alkoxy silane compound of the invention and characterization thereof as well as the preparation method of the compound in more detail.

EXAMPLE 1

Into a three-necked round-bottom flask of 200 ml capacity equipped with a reflux condenser, thermometer and stirrer were introduced 105.0 g (218 mmoles) of a polyfluorinated amine compound of the formula

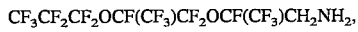
$CF_3CF_2CF_2OCF(CF_3)CF_2OCF(CF_3)CH_2NH_2$, 12.0 g (41.4 mmoles) of 3-iodopropyl trimethoxy silane, 35.0 g of methyl alcohol and 4.2 g of triethyl amine to form a reaction mixture which was heated at 70° C. under reflux of methyl alcohol with agitation for 50 hours to effect the dehydroiodination reaction. After the above mentioned reaction time, the flask was chilled in an ice water bath and the reaction mixture in the flask was admixed with 8.0 g of a methyl alcohol solution of sodium methylate in a concentration of 28% by weight and agitated for 30 minutes followed by removal of methyl alcohol by distillation. The precipitates found in the reaction mixture were removed by filtration and the filtrate was subjected to distillation under reduced pressure to collect 13.4 g of a fraction boiling at 104° C. under a pressure of 10 mmHg.

The thus obtained reaction product was identified to be a polyfluorinated trimethoxy silane compound of the formula

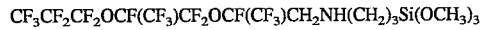
$CF_3CF_2CF_2OCF(CF_3)CF_2OCF(CF_3)CH_2NH(CH_2)_3Si(OCH_3)_3$ from the results of the analyses shown below. The above mentioned yield of the product compound corresponds to 50.8% of the theoretical value.

$^1$H-NMR: δ, ppm (reference to TMS)
0.59 (2H, m) Si—CH$_2$
1.54 (2H, m) CH$_2$—CH$_2$—CH$_2$
2.66 (2H, m) CH$_2$—CH$_2$—NH
3.31 (2H, d) CF—CH$_2$
3.50 (9H, s) O—CH$_3$
$^{19}$F-NMR: δ, ppm (reference to CF$_3$COOH)
−68.4 (1F, m) O—CF—CF$_2$
−54.7 (1F, m) CF—CH$_2$
−53.4 (2F, s) CF$_3$—CF$_2$—CF$_2$
−6.3 to −4.3 (13F, m) CF$_3$, CF$_2$O
Mass spectrometric-gas chromatography:
M/e=643
(calculated molecular weight 643 for C$_{15}$H$_{18}$O$_5$NF$_{17}$Si)
Infrared absorption spectrophotometry:
See FIG. 1.
3420 cm$^{-1}$ (N—H); 1000–1300 cm$^{-1}$ (C—F)

EXAMPLE 2

Into a three-necked round-bottom flask of 500 ml capacity equipped with a reflux condenser, thermometer and stirrer were introduced 150.0 g (382 mmoles) of a polyfluorinated diamine compound of the formula

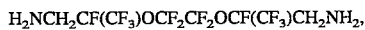
$H_2NCH_2CF(CF_3)OCF_2CF_2OCF(CF_3)CH_2NH_2$, 29.0 g (100 mmoles) of 3—iodopropyl trimethoxy silane, 150.0 g of methyl alcohol and 11.6 g of triethyl amine to form a reaction mixture which was heated at 70° C. under reflux of methyl alcohol with agitation for 48 hours to effect the dehydroiodination reaction. After the above mentioned reaction time, the reaction mixture in the flask was cooled to room temperature and admixed with 15.6 g of a methyl alcohol solution of sodium methylate in a concentration of 28% by weight and agitated for 30 minutes followed by removal of methyl alcohol by distillation. The precipitates found in the reaction mixture were removed by filtration and the filtrate was subjected to distillation under reduced pressure to collect 21.5 g of a fraction boiling at 126° C. under a pressure of 3 mmHg.

The thus obtained reaction product was identified to be a polyfluorinated trimethoxy silane compound of the formula

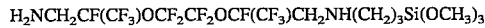
$H_2NCH_2CF(CF_3)OCF_2CF_2OCF(CF_3)CH_2NH(CH_2)_3Si(OCH_3)_3$ from the results of the analyses shown below. The above mentioned yield of the product compound corresponds to 38.8% of the theoretical value.

Figure 2:
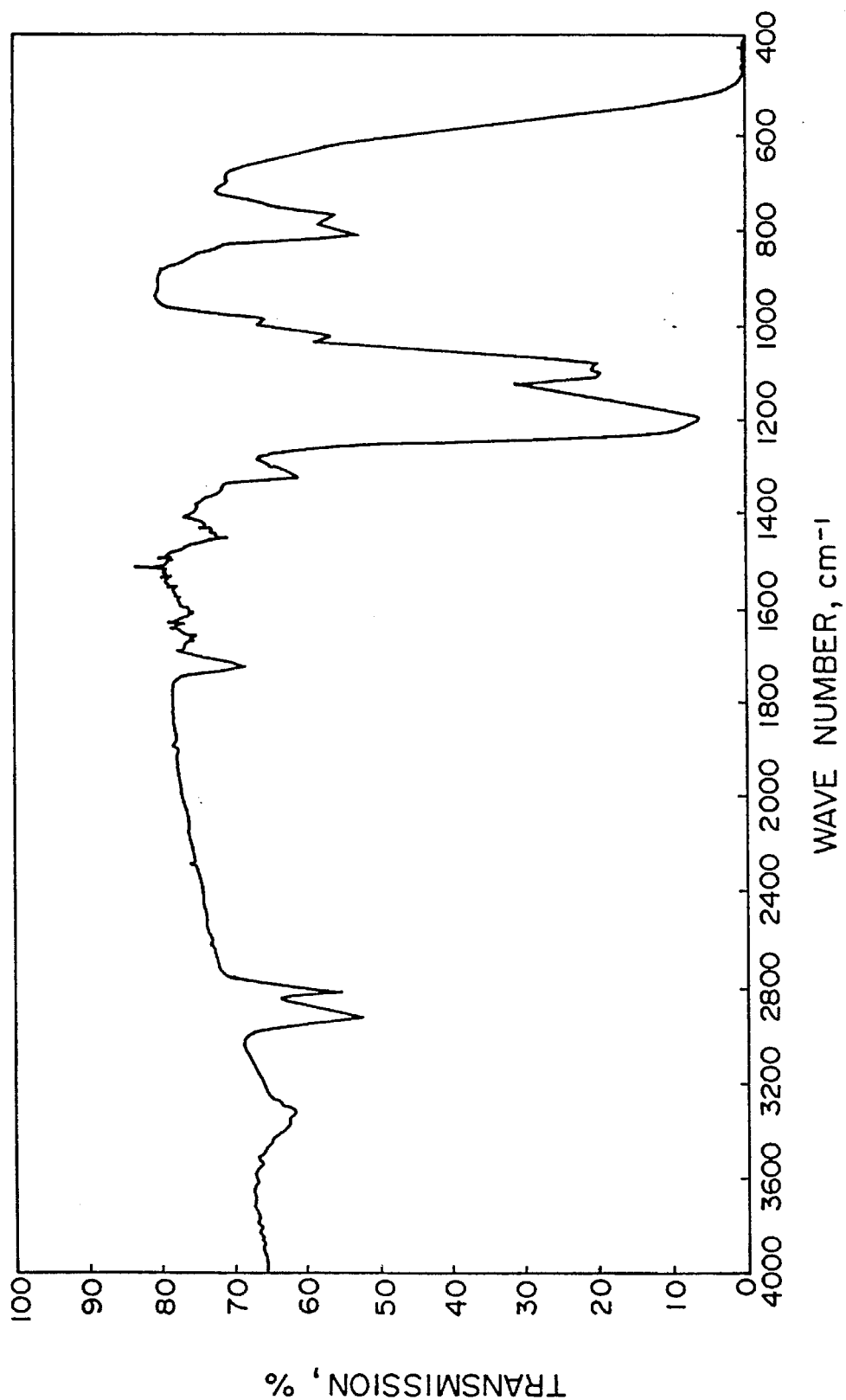

$^1$H-NMR: δ, ppm (reference to TMS)
0.59 (2H, m) Si—CH$_2$
1.55 (2H, m) CH$_2$—CH$_2$—CH$_2$
2.66 (2H, m) CH$_2$—CH$_2$—NH
3.30 (4H, d) CF—CH$_2$
3.50 (9H, s) O—CH$_3$
$^{19}$F-NMR: δ, ppm (reference to CF$_3$COOH)
−58.3 (1F, m) CF—CH$_2$—NH$_2$
−54.7 (1F, m) CF—CH$_2$—NH—CH$_2$
−9.5 to −5.2 (10F, m) CF$_3$, CF$_2$
Mass spectrometric-gas chromatography:
M/e= 554
(calculated molecular weight 554 for C$_{14}$H$_{22}$O$_5$N$_2$F$_{12}$Si)
Infrared absorption spectrophotometry:
See FIG. 2.
3420 cm$^{-1}$ (N—H); 1000–1300 cm$^{-1}$ (C—F)

What is claimed is:

1. A polyfluorocarbon group-containing alkoxy silane compound of the formula

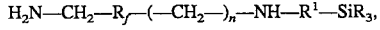
$H_2N—CH_2—R_f—(—CH_2—)_n—NH—R^1—SiR_3$, in which each R is, independently from the others, a monovalent hydrocarbon group having 1 to 10 carbon atoms or an alkoxy group having 1 to 6 carbon atoms with the proviso that at least one of the three groups denoted by R is an alkoxy group, $R^1$ is a divalent hydrocarbon group having 1 to 10 carbon atoms, $R_f$ is a polyfluorinated alkylene group with 1 to 20 carbon atoms or a polyfluorinated etherified alkylene group with 2 to 20 carbon atoms having at least one oxygen atom between two carbon atoms of an alkylene group forming an ether linkage, at least two of the hydrogen atoms therein being substituted by fluorine atoms, and the subscript n is 1 or 2.

2. The perfluorocarbon group-containing alkoxy silane compound of claim 1, wherein each R is independently an alkyl or alkenyl group of 1–10 carbon atoms, phenyl, tolyl, benzyl, 2-phenylethyl or alkoxy or alkoxy-substituted alkoxy group of 1 to 6 carbon atoms.

3. The perfluorocarbon group-containing alkoxy silane compound of claim 1, wherein two of the R groups are alkoxy groups.

4. The perfluorocarbon group- containing alkoxy silane compound of claim 1, wherein all three of the R groups are alkoxy groups.

5. The perfluorocarbon group-containing alkoxy silane compound of claim 1, wherein $R^1$ is an alkylene arylene or combined alkylene and arylene group of 1 to 10 carbon atoms.

6. The perfluorocarbon group-containing alkoxy silane compound of claim 1, wherein $R_f$ is a perfluorinated alkylene or etherified alkylene group.

7. The perfluorocarbon group-containing alkoxy silane compound of claim 1 of one of the following formulae:

$H_2NCH_2CF_2CF_2CH_2-R^1-SiR_3$; $H_2NCH_2CF_2CF_2CF_2CF_2CH_2-R^1-SiR_3$;

$H_2NCH_2CF(CF_3)OCF_2CF_2OCF(CF_3)CH_2-R^1-SiR_3$;

$H_2NCH_2CF(CF_3)OCF_2CF_2CF_2CF_2OCF(CF_3)CH_2-R^1-SiR_3$;

$H_2NCH_2CFOCF_2CF_2OCF_2CH_2-R^1-SiR_3$; and $H_2NCH_2CF_2O(CF_2)_uO(CF_2CF_2)_vOCF_2CH_2-R^1-SiR_3$, in which $R^1$ and R are as defined above, and u and v are each a positive integer with the proviso that u=2v does not exceed 18.

* * * * *